(12) United States Patent
Wissmann et al.

(10) Patent No.: US 7,683,170 B2
(45) Date of Patent: Mar. 23, 2010

(54) METHODS FOR PREPARING IRINOTECAN

(75) Inventors: Friedrich Wissmann, Alzenau (DE); Holger Rauter, Flieden (DE); Silvia Werner, Kahl (DE)

(73) Assignee: W. C. Heraeus GmbH, Hanau (DE)

( * ) Notice: Subject to any disclaimer, the term of this patent is extended or adjusted under 35 U.S.C. 154(b) by 37 days.

(21) Appl. No.: 11/608,946

(22) Filed: Dec. 11, 2006

(65) Prior Publication Data

US 2007/0135471 A1 Jun. 14, 2007

(30) Foreign Application Priority Data

Dec. 13, 2005 (EP) .................. 05027167

(51) Int. Cl.
*C07D 489/00* (2006.01)
(52) U.S. Cl. ....................................... 546/48
(58) Field of Classification Search ................. 546/187, 546/48
See application file for complete search history.

(56) References Cited

U.S. PATENT DOCUMENTS 4,604,463 A 8/1986 Miyaska et al.
7,126,000 B2 * 10/2006 Ogawa et al. .................. 546/92

FOREIGN PATENT DOCUMENTS

| WO | 9631513 | * | 10/1996 |
| WO | 2004/056398 | * | 8/2004 |
| WO | WO 2005/019223 A1 | | 3/2005 |
| WO | 2006/016203 | * | 2/2006 |
| WO | 2006016203 | * | 2/2006 |

OTHER PUBLICATIONS

Hcaplus 115:183643.*
Hcaplus 115: 183643.*
Sawada, et al; "Synthesis and Antitumor Activity of 20(S)-Camptothecin Derivatives: Carbamate-Linked, Water-Soluble Derivatives of 7-Ethyl-10-hydroxycamptothecin"; Chem. Pharm. Bull., 39, pp. 1446-1454 (1991).
European Search Report, Apr. 26, 2006, EP 05027167.

* cited by examiner

*Primary Examiner*—Janet L. Andres
*Assistant Examiner*—Binta Robinson
(74) *Attorney, Agent, or Firm*—Norris McLaughlin & Marcus, P.A.

(57) ABSTRACT

Methods for manufacturing 7-ethyl-10-[4-(1-piperidino)-1-piperidino]-carbonyloxy-camptothecin are described comprising I. reacting a mixture of 1-chlorocarbonyl-4-piperidinopiperidine hydrochloride and 7-ethyl-10-hydroxycamptothecin in a polar aprotic solvent with a base in the presence of catalytic amounts of a N-containing cyclic organic compound having 3 to 20 carbon atoms and optionally in the presence of a water binding agent in an amount which effectively binds any water present in the above reactants and solvents; or II. reacting:
(a) 7-Ethyl-10-hydroxycamptothecin in a polar aprotic solvent with phosgene, trichlormethyl-chloroformate, bis(trichloromethyl)carbonate or a alternative to phosgene and a base in the presence of catalytic amounts of a N-containing cyclic organic compound having 3 to 20 carbon atoms; and
(b) subsequently with piperidinopiperidine and an amine base.

12 Claims, No Drawings

METHODS FOR PREPARING IRINOTECAN

The invention relates to methods for preparing 7-ethyl-10-[4-(1-piperidino)-1-piperidino]-carbonyloxy camptothecin (Irinotecan).

BACKGROUND

U.S. Pat. No. 4,604,463 describes the preparation of 7-Ethyl-10-[4-(1-piperidino)-1-piperidino]-carbonyloxy-camptothecin (I) by condensation of 7-ethyl-10-hydroxy-camptothecin (II) with 1-chlorocarbonyl-4-piperidinopiperidine hydrochloride (III) in pyridine at room temperature.

According to WO200519223 this method leads to coloured impurities in the product. In order to avoid these, 7-Ethyl-10-[4-(1-piperidino)-1-piperidino]-carbonyloxycamptothecin was prepared by condensation of 7-ethyl-10-hydroxycamptothecin of formula

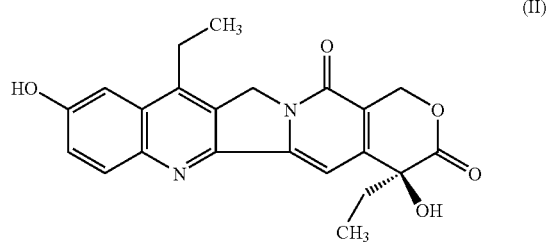

(II)

with 1-chlorocarbonyl-4-piperidinopiperidine hydrochloride of formula

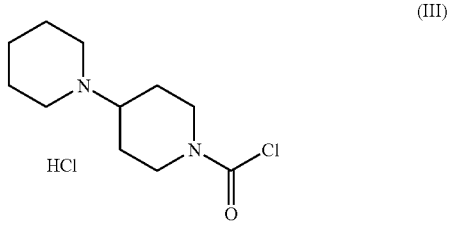

(III)

in a polar aprotic solvent such as acetonitrile and in the presence of 4-dimethyl-aminopyridine. The condensation proceeds in suspension, where the polar aprotic solvent dissolves only 4-dimethylaminopyridine whereas 7-ethyl-10-hydroxycamptothecin and 1-chlorocarbonyl-4-piperidinopiperidine hydrochloride in this polar aprotic solvent remain undissolved. The amount of 1-chlorocarbonyl-4-piperidinopiperidine hydrochloride employed in the condensation reaction is preferably 1.3 to 3 mol, more preferably 1.6 to 1.9 mol, per 1 mol of 7-ethyl-10-hydroxycamptothecin. The amount of 4-dimethylaminopyridine used in the condensation ranges preferably between 1.5 and 4 mol, more preferably between 1.8 and 2.2 mol, per 1 mol of 7-ethyl-10-hydroxycamptothecin. The amount of the polar aprotic solvent used in the condensation is preferably 400 to 600 mol, more preferably 430 to 460 mol, per mol of 7-ethyl-10-hydroxycamptothecin. The condensation is performed preferably at a temperature from 70 to 80° C., more preferably at 73 to 77° C.

SUMMARY

According to the present invention a method for preparing 7-ethyl-10-[4-(1-piperidino)-1-piperidino]-carbonyloxy-camptothecin (I) is disclosed comprising A reacting a mixture of 1-chlorocarbonyl-4-piperidinopiperidine hydrochloride (III) and 7-ethyl-10-hydroxy-camptothecin (II)

B in a polar aprotic solvent

C with a base

D in the presence of catalytic amounts of a N-containing cyclic organic compound having 3 to 20 carbon atoms, and optionally E in the presence of a water binding agent in an amount which effectively binds any water present in 7-ethyl-10-hydroxycamptothecin.

DETAILED DESCRIPTION

The reaction scheme is as follows:

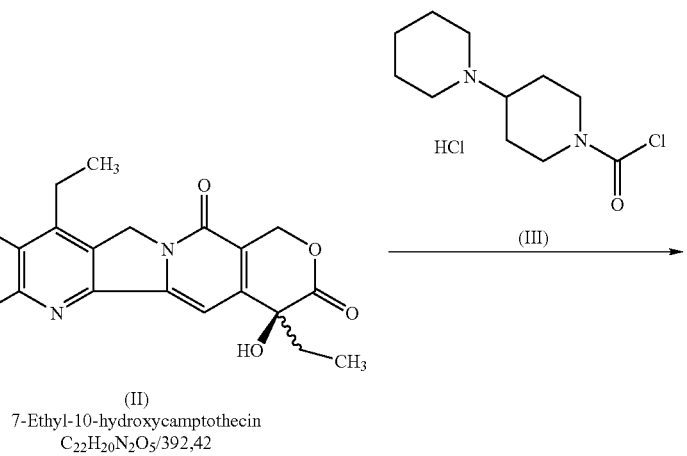

(II)
7-Ethyl-10-hydroxycamptothecin
$C_{22}H_{20}N_2O_5/392,42$

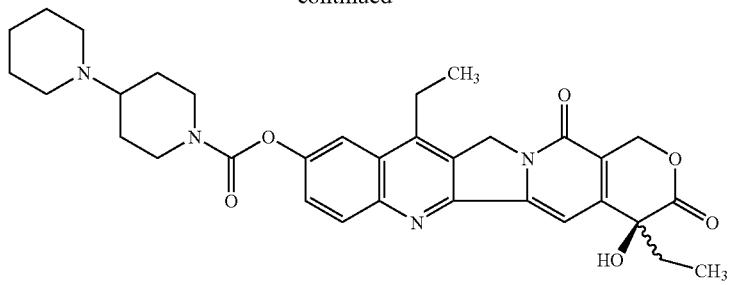

(I)
Irinotecan
$C_{33}H_{38}N_4O_6/586,69$

The amount of base is preferably calculated to be the molar equivalent to about 1.1 times the amount of hydrochloride present during the reaction.

The amount of (III) can be from 1.0 to about 2.3 or more equivalents of (II). However, the more (III) is added, the more impurities will arise. Therefore 1.0 to 1.3 equivalents of (III) are preferred.

Catalytic amounts of the N-containing cyclic organic compound are preferably from about 0.01 to about 0.2 molar equivalents, more preferably about 0.1 eq.

The water binding agent (step E) is applied advantageously when the reactants contain humidity in the form of water.

An advantage of the above-described process is that the reaction temperature can be brought down to 35-40° C., as compared to 70-80° C. in the process of WO2005019223A1.

Examples of polar aprotic solvents are DMF, DMSO, 1,4-dioxane, THF, methylene chloride, chloroform, acetonitrile or mixtures thereof.

The base is preferably an amine, e.g. diisopropylethylamine, triethylamine, pyridine or bases selected from the group of N-containing cyclic organic compounds as described below.

The N-containing cyclic organic compound is preferably selected from the group comprising Dimethylaminopyridine,

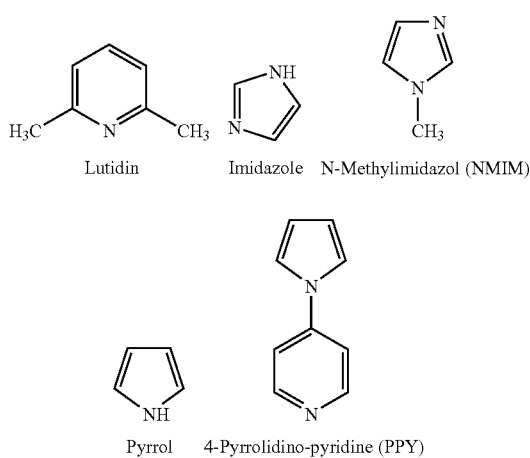

Lutidin   Imidazole   N-Methylimidazol (NMIM)

Pyrrol    4-Pyrrolidino-pyridine (PPY)

1,4-Diazabicyclo[2,2,2-]octan (DABCO)

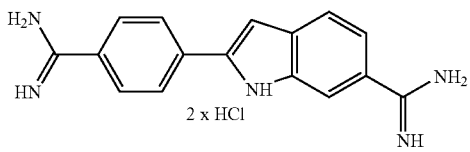

2 x HCl

4'-6-Diamidino-2-phenylindol (DAPI)

The following Example describes a preferred embodiment of the invention (m/m means mass relation):

EXAMPLE 1

A mixture of 25.02 g (0.0637 mol) 7-ethyl-10-hydroxy-camptothecin, 18.72 g (0.07 mmol) of 4-piperidinopiperidi-necarbonylchloride, 0.99 g (6.4 mmol) DABCO and 400 ml dichloromethane is treated with 18.93 g (0.146 mol) N,N-Diisopropylethylamine (DIEA) at 35 to 40° C. After 0.5 h complete conversion (>99%), is observed. Subsequently, the organic layer is washed 3 times with $NH_4Cl$-solution (27%), $KHCO_3$-solution (25%) and NaCl-solution (26%). Active charcoal is added, and the suspension is warmed to reflux for at least 1 h. Charcoal is filtered off and subsequently 800 ml t-Butylmethylether (t-BME) is added within 30 min at reflux. The mixture is cooled to 35-40° C. (precipitation of the product) and stirred for at least 1 h at 35-40° C. The suspension is cooled to 0-5° C., stirred for at least 1 additional hour and subsequently filtered off and dried in vacuo.

The crude product (Irinotecan free base) is crystallized from 2-methoxyethanol.

Yield: 32.9 g (88% of theory) Appearance: yellow, crystalline powder

An alternative procedure is represented in the following reaction scheme:

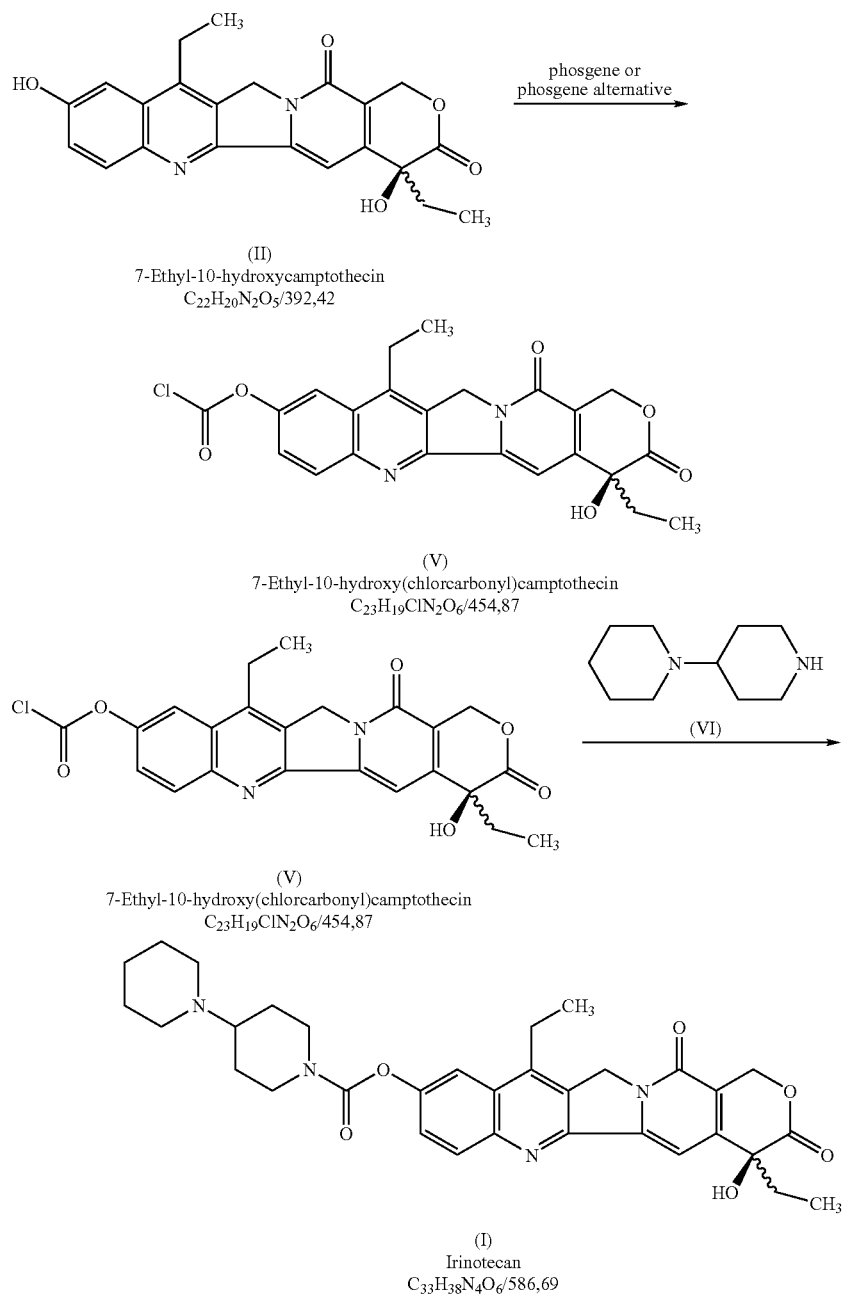

(II)
7-Ethyl-10-hydroxycamptothecin
$C_{22}H_{20}N_2O_5/392,42$ (V)
7-Ethyl-10-hydroxy(chlorcarbonyl)camptothecin
$C_{23}H_{19}ClN_2O_6/454,87$ (V)
7-Ethyl-10-hydroxy(chlorcarbonyl)camptothecin
$C_{23}H_{19}ClN_2O_6/454,87$ (I)
Irinotecan
$C_{33}H_{38}N_4O_6/586,69$ The invention thus further relates to a method for manufacturing 7-ethyl-10-[4-(1-piperidino)-1-piperidino]-carbonyloxy-camptothecin (I) comprising reacting A 7-Ethyl-10-hydroxycamptothecin (II) in a polar aprotic solvent with phosgene, trichlormethyl-chloroformate, bis(trichloromethyl)carbonate, or an alternative to phosgene and a base in the presence of catalytic amounts of a N-containing cyclic organic compound having 3 to 20 carbon atoms B and subsequently with piperidinopiperidine (VI), and an amine base.

The polar aprotic solvent is as described above.

The reaction is carried out preferably at room temperature.

The bases and amine bases are as described above.

The amount of piperidinopiperidine (VI) is preferably from 1.0 to 2.3 equivalents of 7-ethyl-10-hydroxycamptothecin (II), more preferably from 1.0 to 1.7 equivalents.

Examples of phosgene alternatives or substitutes are diphosgene and triphosgene.

This reaction is exemplified as follows:

EXAMPLE 2

4.00 g (10.2 mmol) 7-Ethyl-10-hydroxycamptothecin (purity 80%) are dissolved in 60 ml $CH_2Cl_2$. 2.15 g (16.3 mmol) diisopropylethylamine, dissolved in 10 ml $CH_2Cl_2$, 0.16 g (1 mmol) DABCO and 1.1 g (36 mmol) bis(trichloromethyl) carbonate, dissolved in 10 ml $CH_2Cl_2$ are added at a temperature of 20° C. within 15 min. The solution is stirred for a further 20 min. Then 1.80 g (16 mmol) piperidinopiperidine, dissolved in 10 ml CH$_2$Cl$_2$, and 2.15 g (16.2 mmol) diisopropylethylamine, dissolved in 10 ml CH$_2$Cl$_2$, are added simultaneously within 15 min at 22° C. The resulting clear solution is stirred for 2-4 h at 25° C.

The organic layer is extracted with 2×80 ml saturated NaHCO$_3$ solution and 3×60 ml H$_2$O. The aqueous layers are collected and extracted with 2×40 ml CH$_2$Cl$_2$. The combined organic layers are extracted again with 2×60 ml H$_2$O, dried over 2 g Na$_2$SO$_4$, filtered and concentrated. The residue is recrystallized from 2-methoxyethanol and dried in vacuo.

Yield: 5.1 g 85.2% of theory Appearance: yellow powder

What is claimed is:

1. A method for preparing 7-ethyl-10-[4-(1-piperidino)-1-piperidino]-carbonyloxy-camptothecin comprising reacting a reactants mixture of 1-chlorocarbonyl-4-piperidinopiperidine hydrochloride and 7-ethyl-10-hydroxycamptothecin in a polar aprotic solvent with diisopropylethylamine in the presence of a catalytic amount of a N-containing cyclic organic compound, and optionally in the presence of a water binding agent in an amount which effectively binds any water present in the above reactants and solvent, wherein said polar aprotic solvent is selected from the group consisting of DMF, DMSO, 1,4-dioxane, THF, methylene chloride, chloroform, acetonitrile and mixture thereof, and said N-containing cyclic organic compound is selected from the group consisting of 4-dimethylaminopyridine, lutidine, pyrrole, imidazole, N-methylimidazole, 4-pyrrolidinopyridine, 4',6'-diamidini-2-phenylindole and 1,4-diazabicyclo[2,2,2]octane (DABCO).

2. The method according to claim 1, wherein the N-containing cyclic organic compound is DABCO.

3. The method according to claim 1, wherein a water binding agent is present and the water binding agent is selected from the group consisting of EDC (N-Ethyl-N'-(3-dimethylaminopropyl)carbodiimide hydrochloride), DIC (N,N'-Diisopropylcarbodiimide), DCC (N,N'-Dicyclohhexylcarbodiimide), PPAA (Tris-n-propane-phosphonic acid anhydride), sodium sulphate, magnesium sulphate, sodium hydride and a zeolite-based molecular sieve.

4. The method according to claim 1, wherein the amount of 1-chlorocarbonyl-4-piperidinopiperidine hydrochloride is from 1.0 to 2.3 equivalents of 7-ethyl-10-hydroxycamptothecin.

5. The method according to claim 4, wherein the amount of 1-chlorocarbonyl-4-piperidinopiperidine hydrochloride is from 1.0 to 1.3 equivalents of 7-ethyl-10-hydroxycamptothecin.

6. A method for preparing 7-ethyl-10-[4-(1-piperidino)-1-piperidino]-carbonyloxy-camptothecin comprising reacting:
   (a) 7-Ethyl-10-hydroxycamptothecin in a polar aprotic solvent with phosgene, trichlormethyl-chloroformate, bis(trichloromethyl)carbonate or an alternative to phosgene and diisopropylethylamine in the presence of a catalytic amount of a N-containing cyclic organic compound selected from the group consisting of 4-dimethylaminopyridine, lutidine, pyrrole, imidazole, N-methylimidazole, 4-pyrrolidinopyridine, 4',6'-diamidini-2-phenylindole and 1,4-diazabicyclo[2,2,2]octane (DABCO); and
   (b) subsequently with piperidinopiperidine and an amine base.

7. The method of claim 6, wherein the reaction is carried out at room temperature.

8. The method of claim 6, wherein the solvent is selected from the group consisting of DMF, DMSO, dioxane, THF, methylene chloride, chloroform, acetonitrile and mixtures thereof.

9. The method according to claim 6, wherein the N-containing cyclic organic compound is DABCO.

10. The method according to claim 6, which further comprises recrystallizing the product from 2-methoxyethanol.

11. The method according to claim 6, wherein the amount of 1-chlorocarbonyl-4-piperidinopiperidine hydrochloride is from 1.0 to 2.3 equivalents of 7-ethyl-10-hydroxycamptothecin.

12. The method according to claim 11, wherein the amount of 1-chlorocarbonyl-4-piperidinopiperidine hydrochloride is from 1.0 to 1.3 equivalents of 7-ethyl-10-hydroxycamptothecin.

* * * * *